United States Patent [19]

Chen et al.

[11] Patent Number: 4,573,995
[45] Date of Patent: Mar. 4, 1986

[54] TRANSDERMAL THERAPEUTIC SYSTEMS FOR THE ADMINISTRATION OF NALOXONE, NALTREXONE AND NALBUPHINE

[75] Inventors: Yu-Ling Chen, Cupertino; Leslie L. Chun, Palo Alto; David J. Enscore, Sunnyvale, all of Calif.

[73] Assignee: ALZA Corporation, Palo Alto, Calif.

[21] Appl. No.: 659,122

[22] Filed: Oct. 9, 1984

[51] Int. Cl.⁴ .............................................. A61K 9/00
[52] U.S. Cl. ...................................... 604/896; 424/28; 514/282; 514/785; 604/897; 514/946
[58] Field of Search ................... 604/896, 897, 890; 424/260, 27, 28, 307

[56] References Cited

U.S. PATENT DOCUMENTS

| | | | |
|---|---|---|---|
| 4,141,897 | 2/1979 | Olofson et al. | 546/46 |
| 4,201,211 | 5/1980 | Chandrasekaran et al. | 604/897 |
| 4,435,180 | 3/1984 | Leeper | 604/896 |
| 4,460,372 | 7/1984 | Campbell et al. | 604/897 |
| 4,464,378 | 8/1984 | Hussain | 546/45 |
| 4,493,848 | 1/1985 | LaHann et al. | 424/324 |

*Primary Examiner*—Andrew H. Metz
*Assistant Examiner*—Terryence Chapman
*Attorney, Agent, or Firm*—Steven F. Stone; Paul L. Sabatine; Edward L. Mandell

[57] ABSTRACT

A method for transdermal delivery of naloxone, naltrexone and nalbuphine base through intact skin is described. Preferred embodiments of transdermal therapeutic systems for delivering these drugs and polyethylene glycol monolaurate employ an ethylene vinylacetate matrix containing drug base at a concentration above saturation and polyethylene glycol monolaurate below unit activity. Polyethylene glycol manolaurate is disclosed as a permeation enhancer for the base form of these drugs and is preferably delivered simultaneously with the drug.

33 Claims, 2 Drawing Figures

TRANSDERMAL THERAPEUTIC SYSTEMS FOR THE ADMINISTRATION OF NALOXONE, NALTREXONE AND NALBUPHINE

FIELD OF THE INVENTION

This invention relates to transdermal therapeutic system for the parenteral administration of naloxone, naltrexone and nalbuphine through intact skin.

RELATED PATENT APPLICATIONS

This application is related to the copending coassigned patent application Ser. No. 06/659,121 of like date herewith of Taskovich et al. for Skin Permeation Enhancer Compositions.

BACKGROUND OF THE INVENTION

Naloxone, naltrexone and nalbuphine are known, chemically similar drugs and are described in the 1984 USAN and the USP Dictionary of Drug Names, United States Pharmacopiea Convention, Inc., Rockville, MD pp. 327 and 378 (1983). The therapeutic administration of naloxone and nalbuphine is currently limited to injection or infusion typically from solution of the hydrochloride and naltrexone is under investigation for similar administration. Although various types of transdermal therapeutic systems for delivering a wide variety of drugs are known to the art, such as described in U.S. Pat. Nos. 3,598,122, 3,598,123, 4,379,454, 4,286,592, and 4,317,557, (which are all incorporated herein by reference) for example, none of these patents are directed specifically to systems for the transdermal delivery of either naloxone, naltrexone or nalbuphine. We found that the permeability through skin of these drugs is too low to produce any therapeutic effect from a reasonably sized therapeutic system. When we attempted to increase their permeation through skin by the contemporaneous administration of conventional permeation enhancers we were either unsuccessful in increasing the flux or we observed unacceptable levels of irritation to the skin.

According to this invention we have discovered that the base form of naloxone, naltrexone and nalbuphine can be delivered through intact skin at fluxes capable of producing therapeutic effects if delivered in the presence of permeation enhancing amounts of polyethylene glycol monolaurate (PEGML) and have provided drug/permeation enhancer reservoir compositions and transdermal therapeutic systems incorporating the same which are useful in the transdermal delivery of naloxone, naltrexone and nalbuphine.

It is accordingly an object of this invention to provide transdermal therapeutic systems for the delivery of naloxone, naltrexone and nalbuphine through intact skin.

It is another object of this invention to provide drug reservoir/permeation enhancer compositions for use in the transdermal delivery of naloxone, naltrexone and nalbuphine.

It is another object of this invention to provide a method for the transdermal administration of naloxone, naltrexone and nalbuphine.

These and other objects and advantages will be readily apparent from the following description with reference to the accompanying drawings wherein:

DESCRIPTION OF THE INVENTION

According to our invention we have discovered that therapeutic amounts of naloxone, naltrexone or nalbuphine can be delivered transdermally by topical application of the drug in the base form to the skin in the presence of flux enhancing amounts of polyethylene glycol monolaurate (PEGML). In addition, by appropriate selection of the thermodynamic activity of the drug and the PEGML in the reservoir compositions, the drug can be delivered over extended periods of time without producing unacceptable irritation to the skin. Although the drugs are currently administered by injection in the form of the water soluble hydrochloride, our transdermal systems utilize the drugs in the form of the base, and as used herein the term, "drug" refers to the base form of naloxone, naltrexone and nalbuphine.

Figure 1:
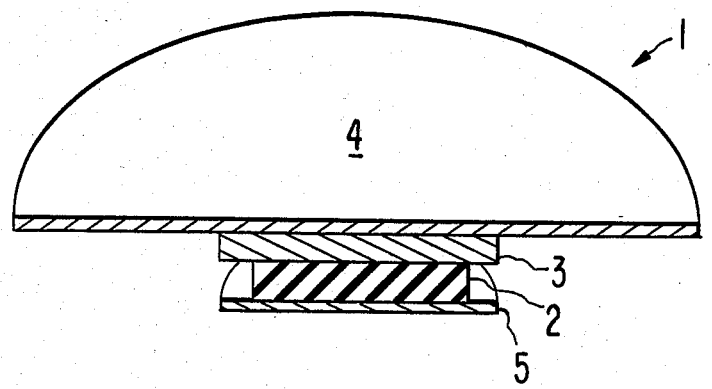
FIG. 1 is a cross-sectional, perspective view through one embodiment of transdermal therapeutic system according to this invention.

Referring now to FIG. 1, a transdermal therapeutic system 1 according to this invention is shown which comprises a drug/permeation enhancer reservoir 2 in the form of matrix having drug and PEGML dispersed therethrough. The reservoir 2 is covered by an impermeable backing 3 which is preferably sized slightly larger in circumference than reservoir 2. Means 4 for maintaining the system on the skin may either be fabricated together with or provided separately from the remaining elements of the system which means in the embodiment of FIG. 1 takes the form of an adhesive overlay. The use of an adhesive overlay with this invention is preferred to the use of an inline adhesive applied to the skin proximal surface of reservoir 2 because PEGML adversely affects the adhesive properties of most pharmaceutically acceptable contact adhesives. For this reason, impermeable backing layer 3 is preferably sized slightly larger than the reservoir 2 to provide a peripheral area around reservoir 2 free of PEGML to prevent adverse interaction between the adhesive in the overlay 4 and any of the PEGML which may seep from under the base of reservoir 2 in use. A strippable release liner 5, adapted to be removed prior to application would normally be included in the packaged product.

Various materials suited for the fabrication of the various layers are disclosed in the aforementioned patents. Due to the solubility characteristics of the drug and PEGML, the matrix is preferably an anhydrous matrix, such as natural or synthetic rubbers, or other polymeric material, thickened mineral oil or petroleum jelly, for example. The preferred embodiment according to this invention is fabricated from an ethylene vinylacetate (EVA) co-polymer of the type described in U.S. Pat. No. 4,144,317, preferably those having a vinylacetate (VA) content in the range of about 28 to 60% VA. The drug is preferably dispersed through the matrix at a concentration in excess of saturation, the amount of the excess being a function of the intended useful life of the system. The PEGML is initially dispersed through the reservoir, preferably at a concentration below unit activity, i.e., below saturation concentrations in the reservoir, and preferably within the range of activity 0.25 to 0.60. Various grades of PEGML are commercially available differing in average molecular weight of the polyethylene glycol (PEG) component. The lower the molecular weight of the PEG component, the greater is the drug flux obtainable. Thus we prefer PEG (200–400) ML for use in our invention.

In addition to the drug and PEGML which are essential to the invention, the matrix may also contain other materials such as dyes, pigments, inert fillers or other conventional components of transdermal therapeutic systems known to the art. In particular, an inert, non-absorbent filler such as titanium dioxide for example, can be added to the matrix in order to reduce the amount of naloxone contained in the unused and in the depleted systems.

Typical reservoir formulations are described in Table 1.

TABLE 1

| Component | % By Weight |
|---|---|
| Drug | 10–35 |
| PEGML | 10–40 |
| Inert Filler or Other Additive | 0–30 |
| EVA (28–60%) | >20 |

Since the drugs are substantially insoluble in EVA, the total loading of in the matrix can be determined based on desired hourly release rates and duration of administration. When the reservoir compositions are fabricated with the initial PEGML activity of approximately 0.50, relatively constant transdermal fluxes within the range of from about 20 to 40 $\mu g/cm^2/hr$ are obtainable. Such fluxes appear to be maintained so long as drug is present at unit activity and the activity of the PEGML remains above about 0.20.

Figure 2:
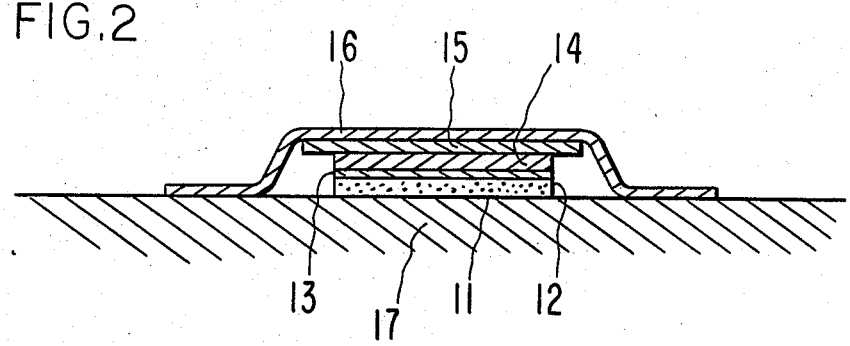
FIG. 2 is a cross-sectional view through another embodiment of transdermal therapeutic system according to this invention.

Referring now to FIG. 2 another embodiment of this invention is shown in place upon the skin 17 of a patient. In this embodiment the transdermal therapeutic system 10 comprises a multilaminate drug/enhancer reservoir 11 having at least two zones 12 and 14. Zone 12 consists of drug/PEGML reservoir substantially as described with respect to FIG. 1. Zone 14 comprises a PEGML reservoir which is preferably made from substantially the same matrix material as used to form zone 12 and which is substantially free of any undissolved drug. A rate-controlling membrane 13 for controlling the release rate of PEGML from zone 14 into zone 12 and from zone 12 to the skin may also be utilized between zones 12 and 14 if desired. Suitable rate-controlling membranes may be formed from materials having a lower permeability to PEGML than the material used to form reservoir zone 14. If an EVA membrane is used in conjunction with EVA matrix the membrane would preferably have a lower VA content than the matrix.

An advantage of the system described in FIG. 2 is that the drug loaded zone 12 is concentrated at the skin surface rather than throughout the entire mass of the reservoir and can function to reduce the amount of drug present in the system while providing an adequate PEGML reservoir for delivery throughout the anticipated system lifetime. The PEGML is preferably incorporated in the reservoir 11 such that its concentration in zone 12 is initially below unit activity and is present in sufficient amounts to maintain the activity within the activity levels described above over the anticipated life of the system. It should be understood that after fabrication of the system the PEGML wll equilibriate throughout reservoir 11. Thus, the equilibrium concentration at the skin surface, is not dependent upon the initial concentration of PEGML in the zone 14 or 12 but on the final equilibrium concentration. Superimposed over the drug enhancer reservoir 11 is an impermeable backing 15 and adhesive overlay 16 as described above with respect to FIG. 1. In addition, a strippable release liner would preferably be provided on the system prior to use as described with respect to FIG. 1 and removed prior to application to the skin 17.

EXAMPLE I

A transdermal therapeutic system according to FIG. 1 was fabricated from 35 wt % naloxone base, 25 wt % PEG 200 ML and 40 wt % EVA (40% VA) by dissolving all components in methyl chloride. The solution was cast onto a glass substrate and dried to remove all solvent. The resulting reservoir composition was removed from the glass substrate and pressed between two siliconized release liners to a thickness of 12 mils and the appropriate sized reservoir cut from the sandwich structure so formed. The appropriately sized plug of reservoir composition so produced was applied to an impermeable, EVA coated, aluminized polyester backing having exterior dimensions slightly larger than that of the reservoir to leave a slight flange about the periphery of the reservoir. The thus formed laminate was then applied on intact human skin by means of an adhesive overlay comprising a microfoam adhesive pad. Systems as described above having a surface area of 1 $cm^2$ were applied to human forearms for a period of 24 hours. They were removed and fresh systems were applied to half of the test sites for another 24 hours. The apparent drug flux through the skin determined from residual drug in the depleted systems was 30.58±8.5 $\mu g/cm^2/hr$ for Day 1 and 30.77±11.72 $\mu g/cm^2/hr$ for Day 2. No observable irritation or erythema was noted 24 hours after removal of the systems.

The therapeutic transdermal delivery rate for naloxone appears to be in the range from about 9 to 30 mg/day with an average of about 15 mg. Thus, systems fabricated as described above having skin contacting surfaces from about 10 to 60 $cm^2$ should be capable of delivering naloxone to patients within the therapeutic dosage range for periods of time as long as 48 hours although larger and smaller systems are also contemplated hereunder.

EXAMPLE II

The in vitro flux of naloxone and nalbuphine base through cadaver skin into an infinite sink at 37° C. from EVA matrices with and without PEGML were measured as follows:

|  | Flux - no PEGML ($\mu g/cm^2/hr$) | Flux 25% PEGML ($\mu g/cm^2/hr$) |
|---|---|---|
| Naloxone | 0.1 | 20 |
| Nalbuphine | <0.1 | 20 |

Accordingly, substitution of nalbuphine base for the naloxone base in systems of Example I should result in nalbuphine delivery at comparable rates. The hourly dosage rates of naloxone and nalbuphine are similar, so similarly sized systems should be suitable for transdermal nalbuphine therapy.

EXAMPLE III

The in vitro skin flux of naloxone and naltrexone base through cadaver skin into an infinite sink at 32° C. from mineral oil donors containing the drug without PEGML and from samples saturated with PEGML were measured as follows:

|  | Flux - no PEGML ($\mu$g/cm$^2$/hr) | Flux - Saturated PEG$_{200}$ML ($\mu$g/cm$^2$ hr) |
| --- | --- | --- |
| Naloxone | 0.2 | 2.1 |
| Naltrexone | 0.1 | 3.5 |

Accordingly substitution of naltrexone base for the naloxone base in the systems of Example I should result in naltrexone delivery at comparable rates. The hourly dosage rates of naloxone and naltrexone are similar so similar sized systems should be suitable for transdermal naltrexone therapy.

Having thus generally described our invention and having provided a specific examples thereof, it will be apparent that various modifications can be made by workers skilled in the art without departing from the scope of the invention which is limited only by the following claims.

We claim:

1. A composition of matter for the transdermal administration of a drug selected from the group consisting of naloxone, naltrexone and nalbuphine and mixtures thereof, comprising a matrix containing the base form of the drug and a skin permeation enhancing amount of polyethylene glycol monolaurate.

2. The composition of claim 1 wherein said drug base is present in an amount in excess of its saturation concentration in the matrix.

3. The composition of claim 1 wherein said polyethylene glycol monolaurate is present at an activity no greater than about 0.60.

4. The composition of claim 1 wherein said matrix comprises an ethylene vinylacetate copolymer.

5. The composition of claim 4 wherein said ethylene vinylacetate copolymer comprises about 28 to 60% vinylacetate.

6. The composition of claim 5 wherein the ethylene vinylacetate comprises 40% vinylacetate and the average molecular weight of the polyethylene glycol component is about 200.

7. The composition of claim 1, 2, 3, 4, 5 or 6 wherein said drug is naloxone.

8. The composition of claim 1, 2, 3, 4, 5 or 6 wherein said drug is naltrexone.

9. The composition of claim 1, 2, 3, 4, 5 or 6 wherein said drug is nalbuphine.

10. A transdermal therapeutic system comprising the composition of claims 1, 2, 3, 4, 5 or 6 in combination with:
    (a) an occlusive backing behind the skin distal surface of said reservoir composition and
    (b) means for maintaining said reservoir composition in drug and polyethylene glycol monolaurate transferring relationship to human skin.

11. A method for the transdermal administration of a drug selected from the group consisting of naloxone, naltrexone and nalbuphine and mixtures thereof which comprises placing a source of the base form of the drug in drug transmitting relationship to the skin in the presence of a drug permeation enhancing amount of polyethylene glycol monolaurate.

12. The method of claim 11 wherein the source of drug is at unit activity.

13. The method of claim 11 wherein said polyethylene glycol monolauroleate is below unit activity.

14. The method of claim 13 wherein the initial activity of said PEGML in said source is within the range of about 0.25–0.60.

15. The method of claim 11 wherein drug is delivered through the skin at a rate of about 20–40 $\mu$g/hr/cm$^2$ for an extended period of time.

16. A method of the transdermal delivery of a drug selected from the group consisting of naloxone, naltrexone, nalbuphine and mixtures therof which comprises delivering the drug in base form through intact skin for an extended period of time at a therapeutic rate.

17. The method of claim 16 wherein the therapeutic rate is in the range of about 20–40 $\mu$g/cm$^2$/hr.

18. The method of claim 16 wherein said drug is naloxone.

19. The method of claim 16 wherein said drug is naltrexone.

20. The method of claim 16 wherein said drug is nalbuphine.

21. A medical device for the transdermal delivery of a material selected from the group consisting of naloxone, naltrexone and nalbuphine comprising in combination:
    (a) reservoir means containing a skin permeable formulation containing said material;
    (b) an occlusive backing behind the skin distal surface of said reservoir means and extending beyond the periphery of said reservoir means; and
    (c) an adhesive overlay disposed on the skin distal surface of said occlusive backing and extending beyond the periphery thereof.

22. The transdermal therapeutic system of claim 21, wherein said drug is naloxone.

23. The transdermal therapeutic system of claim 21, wherein said drug is naltrexone.

24. The transdermal therapeutic system of claim 21, wherein said drug is nalbuphine.

25. A medical device for the transdermal administration of a material selected from the group consisting of naloxone, naltrexone, and nalbuphine through intact skin for an extended period of time at a therapeutic rate substantially greater than 0.1 $\mu$g/cm$^2$/hour, which comprises:
    (a) a unit activity reservoir of a skin permeable form of said material, said reservoir comprising a carrier having said material substantially uniformly distributed there through at a concentration above saturation;
    (b) a reservoir of a skin permeation enhancer for said material, and
    (c) means for maintaining said material reservoir and said permeation enhancer reservoir in material and permeation enhancer transferring relationship to the same area of intact skin.

26. The medical device of claim 25, wherein said permeation enhancer reservoir is combined with said material reservoir.

27. The medical device of claim 25, wherein said permeation enhancer comprises polyethylene glycol monolaurate at an activity no greater than about 0.6, and said reservoir contains polyethylene glycol monolaurate in an amount sufficient to maintain the activity thereof above about 0.25, throughout said extended period of time.

28. The medical device of claim 25 wherein said skin permeable form of said material is the base form and said material reservoir contains sufficient material to maintain the activity at unit activity throughout said extended period of time.

29. The medical device of claim 25, further comprising means for controlling the rate of release of permeation enhancer from said enhancer reservoir to said material reservoir, and said material reservoir is disposed between said rate controlling means and the skin.

30. The medical device of claim 25, wherein said permeation enhancer comprises polyethylene glycol monolaurate and said reservoir contains polyethylene glycol monolaurate at an activity no greater than about 0.6 and in an amount sufficient to maintain the activity above about 0.25 throughout the said extended time period, said material reservoir contains the base form of said material at a concentration above saturation in an amount sufficient to maintain the concentration of said material at least at the saturation level throughout said period.

31. The medical device of claim 25, further comprising an impermeable backing on the skin distal side of said reservoir.

32. A method for the transdermal delivery of a drug selected from the group consisting of naloxone, naltrexone and nalbuphine at a therapeutic rate substantially greater than 0.1 $\mu g/cm^2/hr$ for an extended period of time which comprises:
(a) contacting an area of intact skin with a source of a skin permeable form of said drug at unit activity and a skin permeation enhancer for said drug at a permeation enhancing concentration,
(b) maintaining said source in drug and permeation enhancer transmitting contact with the skin for said extended period of time; and
(c) maintaining the source of said drug at unit activity and said permeation enhancer at a permeation enhancing concentration for said extended period of time.

33. The method of claim 32 wherein said therapeutic rate is in the range of 20–40 $\mu g/hr/cm^2$ of skin.

* * * * *

UNITED STATES PATENT AND TRADEMARK OFFICE
CERTIFICATE OF CORRECTION

PATENT NO. : 4,573,995

DATED : March 4, 1986

INVENTOR(S) : Cheng, et al.

It is certified that error appears in the above-identified patent and that said Letters Patent is hereby corrected as shown below:

In the Heading, "Chen" should be --Cheng--. In Item [75] Inventors, "Chen" should be --Cheng--. In the Abstract, Line 8, "manolaurate" should be --monolaurate--. Column 1, Line 9, "system" should be --systems--; Line 31, "4,317,557" should be --4,314,557--. Column 3, Line 24, insert --drug--, after "loading of"; Line 65, "equilibriate" should be --equilibrate--. Column 5, Line 18, delete "a". Column 6, Line 49, "there through" should be --therethrough--. Column 6, Line 65, "0.25" should be --0.20--. Column 7, Line 16, "0.25" should be --0.20--.

Signed and Sealed this

Fourteenth Day of October, 1986

[SEAL]

Attest:

DONALD J. QUIGG

Attesting Officer

Commissioner of Patents and Trademarks